US00PP33680P2

(12) United States Plant Patent
van Sambeek

(10) Patent No.: US PP33,680 P2
(45) Date of Patent: Nov. 23, 2021

(54) *PHLOX* PLANT NAMED 'DOPHLOFALISTA'

(50) Latin Name: *Phlox paniculata*
Varietal Denomination: Dophlofalista

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/203,625

(22) Filed: Mar. 16, 2021

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

*Primary Examiner* — June Hwu
(74) *Attorney, Agent, or Firm* — C. Anne Whealy

(57) ABSTRACT

A new and distinct cultivar of *Phlox* plant named 'Dophloflalista', characterized by its upright and uniform plant habit; vigorous growth habit and rapid growth rate; relatively freely branching habit; freely flowering habit; flowers with purple and white bi-colored petal lobes; and good garden performance.

1 Drawing Sheet

Botanical designation: *Phlox paniculata.*
Cultivar denomination: 'DOPHLOFLALISTA'.

STATEMENT REGARDING PRIOR DISCLOSURES BY INVENTOR & APPLICANT/ASSIGNEE:

An European Community Plant Breeder's Rights application for the instant plant was filed by the Applicant/Assignee, Dümmen Group B.V. of De Lier, The Netherlands on Jan. 13, 2021, application number 2021/0128. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox paniculata* and hereinafter referred to by the name 'Dophloflalista'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant is a naturally-occurring branch mutation of *Phlox paniculata* 'Barthirtythree', disclosed in U.S. Plant Pat. No. 16,437. The new *Phlox* plant was discovered and selected by the Inventor on a single flowering plant of 'Barthirtythree' in a controlled environment in Aalsmeer, The Netherlands in June, 2016.

Asexual reproduction of the new *Phlox* plant by vegetative cuttings in a controlled environment in Aalsmeer, The Netherlands since June, 2016 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophloflalista'. These characteristics in combination distinguish 'Dophloflalista' as a new and distinct *Phlox* plant:

1. Upright and uniform plant habit.
2. Vigorous growth habit and rapid growth rate.
3. Relatively freely branching habit.
4. Freely flowering habit.
5. Flowers with purple and white bi-colored petal lobes.
6. Good garden performance.

Plants of the new *Phlox* differ from plants of the mutation parent, 'Barthirtythree' primarily in flower color as petal lobes of plants of the new *Phlox* are purple and white bi-colored whereas petal lobes of plants of 'Barthirtythree' are purple in color.

Plants of the new *Phlox* can be compared to plants of *Phlox paniculata* 'Ditosnow', not patented. In side-by-side comparisons, plants of the new *Phlox* and 'Ditosnow' differ in the following characteristics:

1. Plants of the new *Phlox* are more freely branching than plants of 'Ditosnow'.
2. Plants of the new *Phlox* have purple and white bicolored petal lobes whereas plants of 'Ditosnow' have solid white-colored petal lobes.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Dophloflalista' grown in a container.

DETAILED BOTANICAL DESCRIPTION

The aforementioned photograph and following observations, measurements and values describe plants grown during the early summer in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time one week after planting rooted young plants and were 29 weeks old when the photograph and the description were taken. In the following description, color references are made to The Royal Horticultural Society Colour Chart, Second Edition, except where general terms of ordinary dictionary significance are used.

Botanical classification: *Phlox paniculata* 'Dophloflalista'.

Parentage: Naturally-occurring branch mutation of *Phlox paniculata* 'Barthirtythree', disclosed in U.S. Plant Pat. No. 16,437.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and uniform plant habit; vigorous growth habit and rapid growth rate.

*Plant height*.—About 35 cm.

*Plant width* (*spread*).—About 36 cm.

*Lateral branches*.—Branching habit: Relatively freely branching habit; about four primary branches each with about four secondary branches. Length: About 30 cm. Diameter: About 1 cm. Internode length: About 3.5 cm. Strength: Strong. Aspect: Upright to about 50° from vertical. Texture and luster: Smooth, glabrous; glossy. Color: Close to 145A; at the internodes, close to 79A.

Leaf description:

*Arrangement*.—Opposite, simple; decussate and sessile.

*Length*.—About 7.2 cm.

*Width*.—About 3.8 cm.

*Shape*.—Lanceolate.

*Apex*.—Acute.

*Base*.—Cuneate.

*Margin*.—Entire.

*Texture and luster, upper surface*.—Smooth, glabrous; semi-glossy.

*Texture and luster, lower surface*.—Smooth, glabrous; matte.

*Venation pattern*.—Pinnate, reticulate.

*Color*.—Developing and fully expanded leaves, upper surface: Close to 137A; venation, close to 145A. Developing and fully expanded leaves, lower surface: Close to 138A; venation, close to 145C.

Flower description:

*Flower type and flowering habit*.—Single rotate and salverform flowers arranged in compound terminal and lateral panicles; flowers face mostly upright to outwardly depending on position on inflorescence; freely flowering habit with about 57 flowers per inflorescence and about 768 flowers developing per plant during the flowering season.

*Fragrance*.—Slightly fragrant; sweet, pleasant.

*Natural flowering season*.—Plants begin flowering about 19 weeks after planting; plants flower in July in the garden in The Netherlands; flowers persistent.

*Flower buds*.—Height: About 2 cm. Diameter: About 4 mm. Shape: Conical. Texture and luster: Smooth, glabrous; matte. Color: Close to 155D and 84B.

*Inflorescence height*.—About 23 cm.

*Inflorescence diameter*.—About 12 cm.

*Flower diameter*.—About 2.6 cm.

*Flower depth*.—About 1.6 cm.

*Flower throat diameter*.—About 4 mm.

*Flower tube length*.—About 1.8 cm.

*Flower diameter, proximally*.—About 4 mm.

*Petals*.—Quantity per flower: Typically five in a single whorl; petals fused at the base into a narrow tube. Lobe length: About 1.2 cm. Lobe width: About 1.1 cm. Lobe shape: Obovate. Lobe apex: Rounded. Lobe margin: Entire, not undulate. Lobe texture and luster, upper and lower surfaces: Smooth, glabrous; matte. Throat texture: Smooth, glabrous. Tube texture: Pubescent. Color: Lobe, when opening and fully opened, upper surface: Close to 82A; towards the margins, close to 155D; venation, similar to lamina colors; with development, mostly 155D with center, close to 84B. Lobe, when opening and fully opened, lower surface: Close to 84B; towards the margins, close to 155D; venation, similar to lamina colors; with development, mostly 155D with center, close to 84C. Throat: Close to 77A; venation, close to 77A. Tube: Close to 77A; venation, close to 77A.

*Sepals*.—Quantity per flower: Typically five in a single whorl, fused towards the base; calyx, tubular. Length: About 9 mm. Width: About 1 mm. Shape: Subulate. Apex: Acute. Margin: Entire. Texture and luster, upper surface: Pubescent; semi-glossy. Texture and luster, lower surface: Pubescent; glossy. Color: When opening, upper and lower surfaces: Close to 144A tinged with 83A. Fully opened, upper and lower surfaces: Close to 144A tinged with 83A.

*Peduncles*.—Length: About 3 cm. Diameter: About 1 mm. Strength: Moderately strong. Aspect: About 40° from lateral branch axis. Texture and luster: Smooth, glabrous; glossy. Color: Close to 145A.

*Pedicels*.—Length: About 5 mm. Diameter: About 5 mm. Strength: Weak. Aspect: Up to 40° from peduncle axis. Texture and luster: Smooth, glabrous; glossy. Color: Close to 145A.

*Reproductive organs*.—Stamens: Quantity per flower: Typically five. Filament length: About 2 mm. Filament color: Close to 77A. Anther size: About 1 mm by 2 mm. Anther color: Close to 8D. Pollen amount: Abundant. Pollen color: Close to 155A. Pistils: Quantity per flower: One. Pistil length: About 2 cm. Stigma diameter: About 2 mm. Stigma shape: Three-parted. Stigma color: Close to 145D. Style length: About 1.7 cm. Style color: Close to 145D. Ovary color: Close to 145A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from about −37° C. to about 35° C.

Pathogen & pest resistance: To date, plants of the new *Phlox* have not been observed to be resistant to pathogens and pests common to *Phlox* plants.

It is claimed:

1. A new and distinct *Phlox* plant named 'Dophloflalista' as illustrated and described.

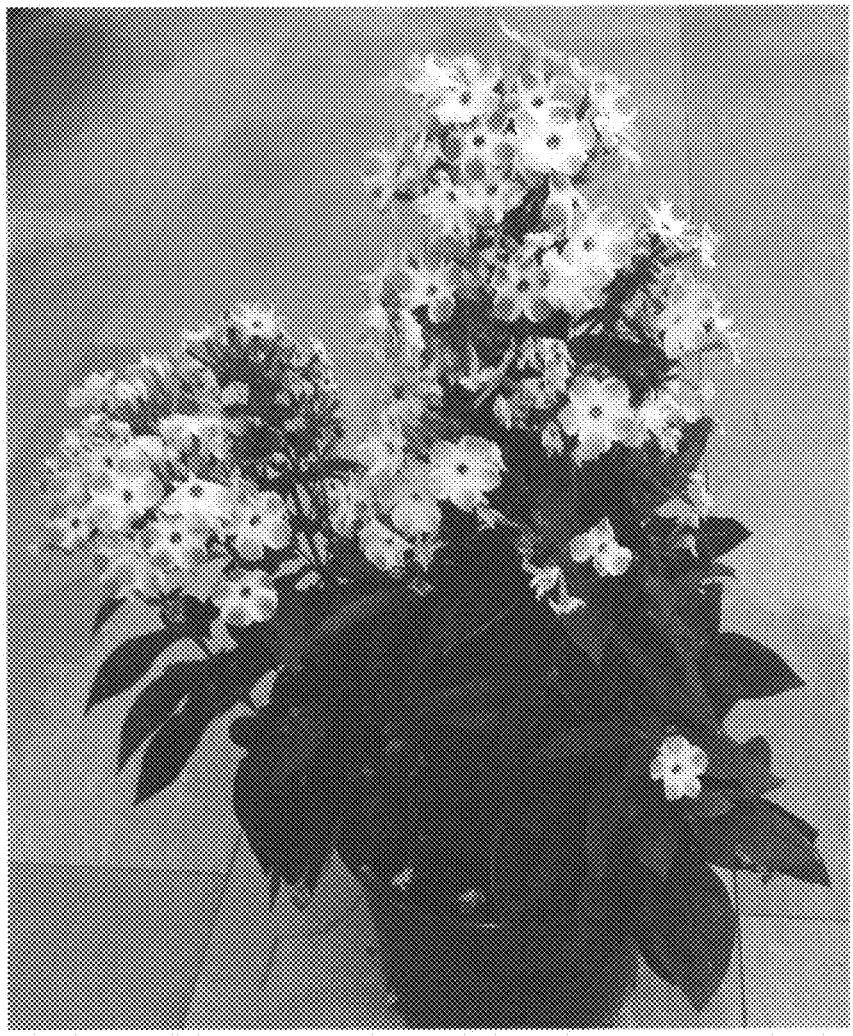

* * * * *